United States Patent [19]
Mollet et al.

[11] Patent Number: 6,150,139
[45] Date of Patent: *Nov. 21, 2000

[54] BACTEROCIDE COMPOSITIONS AND THEIR PREPARATION FROM MICROCOCCUS VARIANS

[75] Inventors: Beat Mollet, Mollie-Margot; John Peel, Lully; David Pridmore; Nadji Rekhif, both of Lausanne; Suri Bruno, Bubendorf, all of Switzerland

[73] Assignee: Nestec S.A., Vevey, Switzerland

[*] Notice: This patent is subject to a terminal disclaimer.

[21] Appl. No.: 09/257,710

[22] Filed: Feb. 25, 1999

Related U.S. Application Data

[63] Continuation of application No. 08/693,353, Aug. 6, 1996.

[30] Foreign Application Priority Data

Aug. 7, 1995 [EP] European Pat. Off. .............. 95810497

[51] Int. Cl.$^7$ .............................. C12P 21/02; C12N 1/22; C07K 14/305
[52] U.S. Cl. ........................ 435/71.2; 435/252.1; 530/324
[58] Field of Search ..................... 435/117, 243, 435/253.4, 71.2, 252.1; 530/324, 300, 344, 325, 320

[56] References Cited

U.S. PATENT DOCUMENTS 5,683,890  11/1997  Germond et al. ....................... 435/69.1

FOREIGN PATENT DOCUMENTS 0643136  3/1995  European Pat. Off. .

OTHER PUBLICATIONS

Piard, et al., "Structure, Organization, and Expression of the lct Gene for Lacticin 481, a Novel Lantibiotic Produced by *Lactococcus lactis*" The Journal of Biological Chemistry vol. 286, pp. 16361–16368 (1993).

Piard, et al., "Purification and Partial Characterization of Lacticin 481, a Lanthionine–Containing Bacteriocin Produced by *Lactococcus lactis* subsp. *lactis* CNRZ 481", Applied and Environmental Microbiology, vol. 58, pp. 279–284 (1992).

Larsen, et al., "Antimicrobial activity of lactic acid bacteria isolated from sour doughs: purification and characterization of bavaricin A, a bacteriocin produced by *Lactobacillus bavaricus* M1401", Journal of Applied Bacteriology, 1993, 75, 112–122.

Cantoni, et al., "Batterioocine Da Micrococcaceae", Industrie Alientari XXXI (1992), pp. 660–665 and translation thereof commissioned by the USPTO and entitled, "Bacteriocins from Micrococcaceae".

Tagg, et al., "Bacteriocins of Gram–Positive Bacteria" 1976, Bacteriol Rev., vol. 40, 1976, pp. 722–756.

Cundliffe, et al., "Inhibition of Ribosomal A Site Functions by Sporangiomycin and Micrococcin", Antimicrobial Agents and Chemotherapy, Jul. 1975, pp. 1–4, vol. 8, No. 1.

Heatley, et al., "The Assay of Micrococcin, an almost Insoluble Antibiotic", *J. gen. Microbiol.* 6, 30–40, 1952.

Heatley, et al., "The Preparation and Some Properties of Puriified Micrococcin", Biochem. J. 50:247–253, 1951.

Su, "Antibiotic–Producing Organisms in Faeces and Sewage", Br. J. Exp. Pathol. 29:466–473, 1948.

Su, "Micrococcin. An Antibacterial Substance Formed by a Strain of Micrococcus", Br. J. Exp. Pathol. 29:473–481, 1948.

Medline database abstract, Accession No. 80079859, abstract of Egorov, et al., "Procedure for isolating nisin from *Streptococcus lactis*", Prikladnaia Biokhimiia I Mikrobiologiia 15:712–714 (1979).

*Primary Examiner*—Karen Cochrane Carlson
*Assistant Examiner*—Gabriele E. Bugaisky
*Attorney, Agent, or Firm*—Vogt & O'Donnell, LLP

[57] ABSTRACT

A bacteriocin having activity against bacteria including *Listeria monocytogenes* is obtained by culturing cells of a strain of *Micrococcus varians*, particularly cells of deposited strains CNCM I-1586 and CNCM I-1587, to obtain cultured cells and a supernatant and by separating the supernatant from the cultured cells to obtain the supernatant which contains the bacteriocin which, in turn, may be isolated from the supernatant.

10 Claims, No Drawings

BACTEROCIDE COMPOSITIONS AND THEIR PREPARATION FROM MICROCOCCUS VARIANS

CROSS-REFERENCE TO RELATED APPLICATION

This application is a continuation of application Ser. No. 08/693,353 which was filed Aug. 6, 1996.

BACKGROUND OF THE INVENTION

The present invention relates to a bacteriocin, to a strain which produces this bacteriocin, to a process for preparing this bacteriocin, and to the use of this bacteriocin and/or a strain producing this bacteriocin in the manufacture of foodstuffs and cosmetics.

STATE OF THE ART

Bacteriocins have been isolated from numerous Gram-positive and Gram-negative bacteria. Bacteriocins are molecules which are essentially proteinaceous in nature and which possess a bactericidal effect and, for this reason, a bacteriocin provokes an antagonistic reaction between the bacterium which produces it and one or more different bacterial species. Furthermore, the inhibition spectrum of a bacteriocin is often limited to the species which are closely related to the bacterial species which produces it.

Bacteriocins have, in particular, been demonstrated in lactic acid bacteria. For example, EP 0643136 (Société des produits Nestlé) describes the identification of two bacteriocins from *Streptococcus thermophilus*. Similarly, a bacteriocin has been isolated from *Lactococcus lactis* (App. and Env. Microbio. 58, 279–284, 1992; J. or Bio. Chem. 268, 16361–16368, 1993).

However, to date, no bacteriocin is known which is derived from *Micrococcus varians*. *Micrococcus varians* is now much used within the foodstuff sphere, in particular in the fermentation of meat for the purpose of manufacturing delicatessen products such as salamis and sausages, for example. It should, therefore, be very useful to have available a bacteriocin-producing strain in order to combat pathogenic agents.

The object of the present invention is to respond to this need.

SUMMARY OF THE INVENTION

To this end, the present invention produces a bacteriocin which is prepared and obtained from *Micrococcus varians*, which bacteriocin has agar well incubation inhibition test activity against at least one of Lactobacillus, Streptococcus, Enterococcus, Listeria, Bacillus, Clostridia and Staphylcoccus. Further to this end, the bacteriocin according to the present invention is a bacteriocin from *Micrococcus varians*, which bacteriocin exhibits the amino acid sequence SEQ ID NO:1 or any amino acid sequence differing from the sequence SEQ ID NO:1 by one substitution, one deletion and/or one insertion of from 1 to 4 amino acids.

Furthermore, any nucleotide fragment encoding this bacteriocin, in particular the nucleotide fragment exhibiting the sequence SEQ ID NO:2, also comes within the scope of the present invention.

Similarly, the strain according to the present invention is a *Micrococcus varians* strain which produces this bacteriocin, in particular the *Micrococcus varians* strains CNCM I-1586 and CNCM I-1587.

In the process for preparing the bacteriocin according to the present invention, a *Micrococcus varians* strain which produces the bacteriocin, in particular the strain CNCM I-1586 or the strain CNCM I-1587, is cultured, in a medium and under conditions which are favourable for growth, so as to obtain a culture medium containing from $10^7$ to $10^{11}$ organisms of this strain per ml, after which the supernatant is isolated from the resulting culture by separating the supernatant from the cultured cells to obtain a supernatant containing the bacteriocin, and to effect separation, the resulting culture is centrifuged and a supernatant extract containing the bacteriocin is obtained. The supernatant may be concentrated to obtain a concentrate comprising the bacteriocin, and the bacteriocin may be isolated from the supernatant and concentrated by dehydration to obtain a powder, and an isolated and purified bacteriocin may be obtained from the supernatant and concentrate and may be dehydrated.

Finally, the use of the *Micrococcus varians* bacteriocin according to the invention comprises using its nucleotide sequence, as well as its signal sequence, and using the supernatant extract containing the bacteriocin, and a *Micrococcus varians* strain which produces the bacteriocin for preparing foodstuffs and cosmetics.

DETAILED DESCRIPTION OF THE INVENTION

In that which follows, the bacteriocin according to the present invention will be termed "variacin".

Within the meaning of the present invention, an arbitrary unit (au) is defined as the inverse of the value of the largest dilution at which a sample still exhibits a bactericidal effect in the test which is known to the skilled person as the "agar well test".

Within the meaning of the present invention, the term "fragment" or "DNA fragment" is to be understood to mean a single-stranded or double-stranded DNA fragment which is partially or entirely coding and which can be synthesized, replicated in vitro by, for example, the known polymerase chain reaction method, or replicated in vivo in a bacterium of the *Escherichia coli* type, for example.

Within the meaning of the present invention, a "homologous fragment" is understood to mean any fragment which only differs form the fragments according to the invention by the substitution, deletion or insertion of a small number of bases. Within this context, two DNA fragments which encode one and the same polypeptide, due to the degeneracy of the genetic code, will, in particular, be regarded as being homologous. That fragment will also be regarded as being an homologous fragment which exhibits more than 80% homology with the fragments according to the invention. In this latter case, the homology is determined by the ratio between the number of bases in a homologous fragment and the number in a fragment according to the invention.

Finally, within the meaning of the present invention, "homologous fragment" is also understood to mean any fragment which is able to hybridize with the fragments according to the present invention by the Southern blot method (Sambrook et al., Molecular Cloning, A Laboratory Manual, Cold Spring Harbor Laboratory Press, U.S.A., 1989, chapter 9.31 to 9.58). Preferably, the hybridization is carried out under rigorous or stringent conditions so as to avoid non-specific hybridization or hybridizations which are relatively unstable.

A proteinaceous factor, in this instance a bacteriocin possessing a powerful bactericidal effect, has been isolated from the strains CNCM I-1586 and CNCM I-1587. This bacteriocin, which is derived from *Micrococcus varians* and which consequently exhibits the amino acid sequence SEQ ID NO:1, which is described in the sequence list below, has been termed variacin.

In view of the interest afforded by variacin, the invention also relates to any bacteriocin which possesses an amino acid sequence which differs from the sequence SEQ ID NO:1 by one substitution, one deletion and/or one insertion of from 1 to 4 amino acids. Thus, the said bacteriocin, which exhibits an amino acid sequence differing from the sequence SEQ ID NO:1 by one substitution, one deletion and/or one insertion of from 1 to 4 amino acids, may have an inhibition spectrum for a bacterial genus or bacterial species which is wider than that of the said variacin, for example.

It has also been possible to select a chromosomal nucleotide fragment encoding the variacin according to the invention from the two strains CNCM I-1586 and CNCM I-1587. The said fragment exhibits the sequence SEQ ID NO:2 given in the sequence list below.

In view of the interest afforded by the present invention, the invention also relates to any nucleotide fragment which encodes the variacin according to the present invention, in particular to nucleotide fragments which are homologous to or which hybridize with the sequence SEQ ID NO:2.

In particular, the invention relates to nucleotides 88 to 153 of the sequence SEQ ID NO:2, encoding the signal peptide of the variacin, to nucleotides 154 to 228 of the sequence SEQ ID NO:2, encoding the secreted variacin according to the present invention, and/or to nucleotides 88 to 228 of the sequence SEQ ID NO:2, encoding the bacteriocin fused to its signal peptide.

The present invention relates also to the bacteriocin fused to its signal peptide which exhibits the amino acid sequence SEQ ID NO:3, which is described in the sequence list below.

The fragment encoding the secreted variacin may be advantageously used to express the variacin according to the present invention in a plant or in a microorganism other than *Micrococcus varians*. To this end, nucleotides 154 to 228 of the sequence SEQ ID NO:2 can be cloned into an expression vector downstream of a promoter or of a signal sequence and upstream of a terminator, while paying due regard to the reading frame, and the said vector can then be introduced into a plant, a bacterium or a yeast so as to increase their spectrum of inhibition towards certain bacteria, for example.

Use can be made of the signal sequence according to the invention by fusing nucleotides 88 to 153 of the sequence SEQ ID NO:2 to a gene of interest, while paying due regard to the reading frame, and by then cloning the whole into a *Micrococcus varians* expression vector, so as to enable the protein encoded by the said gene of interest to be expressed and secreted in *Micrococcus varians*, for example.

Nucleotides 88 to 228 of the sequence SEQ ID NO:2 can be cloned into a *Micrococcus varians* expression vector and introduced into another strain of *Micrococcus varians* so that this latter strain produces the variacin according the present invention.

In addition, the *Micrococcus varians* strain which contains, integrated into its genome or by means of an expression vector, a DNA fragment encoding the variacin according to the invention is also part of the subject-matter of the present invention. In particular, the *Micrococcus varians* strains which were deposited on Jun. 7, 1995, in accordance with the Budapest Treaty, in the Collection National de Cultures de Microorganismes [National collection of microorganism cultures], INSTITUT PASTEUR, 25 Rue du Docteur Roux, F-75724 PARIS CEDEX 15, France, where they were given the deposition numbers CNCM I-1586 and CNCM I-1587, are part of the subject-matter of the present invention.

*Micrococcus varians* bacteria are Gram-positive, catalase-positive, aerobic bacteria which are permanently immobile. They are spherical in shape and are found in the form of tetrads which are arranged irregularly. *Micrococcus varians* colonies are coloured yellow on BHI medium. The optimum temperature for growing the said strains is 25–37° C. Strains CNCM I-1586 and CNCM I-1587, which are part of the subject-matter of the present invention, metabolize both glucose and fructose. The CNCM I-1587 strain additionally metabolizes sucrose and furanose. In addition, strain CNCM I-1586 harbours two plasmids, of 4 and 12 kb, while strain CNCM I-1587 only harbours a single plasmid of 7 kb.

The culture supernatants of strains CNCM I-1586 and CNCM I-1587 exhibit a relatively wide inhibition spectrum with regard to the growth of other bacteria. The following may be included, by way of example, among the bacteria which are sensitive to the said supernatants: *Lactococcus lactis, Lactobacillus helveticus, Lactobacillus delbrueckii subsp. bulgaricus, Lactobacillus delbrueckii subsp. lactis, Lactobacillus delbrueckii subsp. delbrueckii, Lactobacillus acidophilus, Lactobacillus johnsonii, Lactobacillus plantarum, Lactobacillus sake, Lactobacillus curvatus, Leuconostoc carnosum, Leuconostoc mesenteroides subsp. mesenteroides, Streptococcus thermophilus, Listeria monocytogenes, Enterococcus faecalis subsp. faecalis,* the spores and vegetative cells of *Bacillus subtilis, Bacillus cereus, Bacillus polymyxa, Bacillus circulans, Bacillus pumulus* and *Bacillus liqueniformis,* and the Clostridia.

Preferably, in the process for preparing the variacin, a *Micrococcus varians* strain which produces the said bacteriocin is cultivated, in a medium and under conditions which are favourable for growth, so as to obtain a culture medium containing from $10^7$ to $10^{11}$ organisms of said strain per ml, after which the resulting culture is centrifuged and a supernatant extract containing the said bacteriocin is obtained.

In order to produce this extract, the *Micrococcus varians* strain according to the present invention which produces the variacin, in particular strain CNCM I-1586 or strain CNCM I-1587, can be cultured in a medium and under conditions which are favourable for the growth of *Micrococcus varians*. To this end, cultivation can take place, in particular, in BHI medium, at 25–37° C. under aerobic conditions and with shaking, until a concentration of $10^7$–$10^{11}$ organisms per ml of medium is obtained, for example. The standard culture which is thus obtained is centrifuged at 4000–6000 g and the supernatant extract containing the said bacteriocin is collected.

The present invention also relates to the use of variacin, in particular in extract form, or the use of a *Micrococcus varians* strain which produces this bacteriocin, for preparing foodstuffs and cosmetics.

A culture of one the said *Micrococcus varians* strains according to the present invention may, in particular, be used in the fermentation of meat in order to prepare salami so as to combat contamination with Clostridia, for example.

Variacin, in crude extract or purified form, may be used, when added to the leaven which is obtained employing bacteria which are resistant to the said variacin, in the preparation of cheeses, in particular cheeses of the mozzarella type, in order to avoid the holes which are produced by *Bacillus polymixa* whose spores survive the fermentation, and of the vacherin type in order to combat contamination with *Listeria monocytogenes,* for example.

Variacin, in particular in crude extract or purified form, or one of the two strains, may be used as an additive or agent which is active against pathogenic bacteria in the preparation of dessert mousses such as pasteurized custards, so as to combat the growth of spores such as of Clostridia and Bacillus cereus, or of bacterial strain such as Listeria, for example.

In addition, variacin, in crude extract or purified form, or one of the two strains, may be used as an additive or agent which is active against pathogenic bacteria in the preparation of cosmetics, such as moisturizing creams or deodorants, so as to combat pathogenic bacteria of the skin, for example.

ILLUSTRATIVE DESCRIPTION OF VARIACIN CHARACTERISTICS AND ACTIVITY

The variacin according to the present invention is characterized in more detail below with the aid of various microbiological, biochemical and genetic findings which illustrates its properties. The percentages are given by weight.

Unit of antibacterial activity—"agar well test"

Within the context of the present exposition, bactericidal activity is defined in terms of arbitrary units.

A supernatant of a standard culture of *Micrococcus varians* according to the present invention, which supernatant is prepared, for example, under the conditions described in Example 1, typically exhibits an activity of 640 au/ml. Similarly, a concentrate of said supernatant, which concentrate is prepared, for example, under the conditions described in Example 2, typically exhibits an activity of approximately 24000 au/ml.

The said agar well test is used to determine whether a sample still displays bactericidal activity at a given dilution value.

In order to do this, 15 ml of MRS agar medium containing an indicator strain at a concentration of $10^5$–$10^6$ CFU/ml are inoculated into a Petri dish. A strain which is sensitive to variacin, in this case the strain *Lactobacillus bulgaricus* (YL 5) or the strain *Lactobacillus helveticus* (N2), for example, is used as the indicator strain.

Holes of 5 mm in diameter are bored in the culture medium. The samples of the supernatant or of the supernatant concentrate to be tested are poured into the holes at the rate of 50 μl per hole. The dish is preincubated at 4° C. for 2 h and then incubated overnight at either 30° C. or 37° C. depending on the indicator strain employed. Following the incubation, the indicator strain has grown and inhibition halos are visible. The dilution value at which a sample no longer exhibits bactericidal activity is the dilution value starting from which an inhibition halo is no longer discerned.

Inactivation by enzymes

The said agar well test is used to determine whether the variacin which has been isolated in accordance with the present invention is inactivated in the presence of a proteolytic enzyme or in the presence of catalase.

In order to do this, enzyme is added, at the rate of 5 mg/ml, to a concentrate of the culture supernatant described in Example 2. The enzyme is allowed to act at the incubation temperature for 60 min before the sample is deposited in the agar well test well.

A control is prepared in parallel using the same concentrate at pH 7 and without the addition of enzyme. This control sample is incubated at 37° C. for 60 min before it is deposited in the agar well test well for the purpose of comparing the inhibition halos obtained in the presence of enzyme with the inhibition halo of the control. The diameter of the control inhibition halo is 27 mm.

Table I below gives the results which were obtained with the enzymes which were tested using the indicator strain *Lactobacillus helveticus* (N 2). In this table, as in Table II, the enzyme is designated by its type, the name of the supplier and the supplier's catalogue number. The numeral 0 indicates that there is no longer any halo, in other words that the bactericidal activity of the variacin has been compromised by incubating the latter with the enzyme. The numeral 27 indicates that there is still a halo of 27 mm, corresponding to the full bactericidal activity of the variacin.

TABLE I

| Enzymes | Incubation temperature (° C.) | Inactivation (mm) |
|---|---|---|
| Catalase (SIGMA C-10) | 30 | 27 |
| Pronase E (SIGMA P-8038) | 37 | 0 |
| Proteinase K (MERCK 1000 144) | 37 | 0 |
| Ficin (SIGMA F-3266) | 37 | 0 |

Table II below gives the results which were obtained with the enzymes which were tested using the indicator strain *Lactobacillus bulgaricus* (YL 5).

TABLE II

| Enzymes | Incubation temperature (° C.) | Inactivation (mm) |
|---|---|---|
| Catalase (SIGMA C-10) | 30 | 27 |
| Pronase E (SIGMA P-8038) | 37 | 0 |
| Proteinase K (MERCK 1000 144) | 37 | 0 |
| Ficin (SIGMA F-3266) | 37 | 0 |

The results given in Tables I and II show that all the proteolytic enzymes suppress the bactericidal activity of the variacin. These results demonstrate the fact that variacin is proteinaceous in nature and that this proteinaceous moiety is involved in the bactericidal activity.

The fact that catalase is not found to exert any influence on the bactericidal activity of the variacin also demonstrates that inhibition of the growth of the two indicator strains is not due to the antibacterial activity of $H_2O_2$, which is known to have a similar activity to that of the bacteriocins, since $H_2O_2$ would have been degraded by the catalase.

Inhibition spectrum of the culture supernatant containing the variacin

The agar well test is used to determine whether the bactericidal activity of the culture supernatant containing the variacin according to the present invention exhibits an activity which is inhibitory to the growth of the different strains of spores and bacteria. The inhibition spectrum of the supernatant is thus determined.

In order to carry out these assays, 15 ml of a standard medium, which is inoculated with 15 μl of a culture of the strain to be tested, which culture was prepared during the preceding night, are poured into Petri dishes so as to obtain a bacterial concentration of $10^5$–$10^6$ per ml of standard medium. The standard medium is the medium which is favourable to the growth of the strain to be tested.

Furthermore, when the strain to be tested has to grow from spores, $10^5$–$10^6$ spores are inoculated per ml of covering medium.

A hole of 5 mm in diameter is bored in each Petri dish. A sample of 50 μl of culture supernatant, as described in Example 1, is deposited therein. The dishes are preincubated at 4° C. for 2 h and are then incubated at a temperature which is favourable to the growth of the strain under test for the time which is required for the strain to cover the plate with a visible bacterial lawn.

The effect, or the degree of inhibition, herein the "agar well incubation inhibition activity," is characterized by the diameter of the observed inhibition halo. The inhibition is regarded as being very strong (++++) if the halo exhibits a diameter of (18–28 mm, strong (+++) if the diameter is 10–17 mm, average (++) if the diameter is 5–9 mm, weak (+) if the diameter is 1–4 mm, and zero (–) if no halo is observed.

32 strains of lactic acid bacteria of different species and subspecies are tested in this way and it is noted that none of them is resistant to the supernatant. The detailed results of these tests are presented in Table III below. In Table III, as in the following tables, the strain designation or strain no. indicated in the no. which is attributed to it in the Nestlé collection (Address: NESTEC S.A., Centre de Recherche, Vers-chez-les-Blanc, CH-1000 Lausanne 26, Switzerland). The temperature which is indicated in the incubation temperature during the test. The medium which is indicated is the standard medium favourable to the growth of the strain to be tested.

TABLE III

| Species | No. | T (° C.) | Media | Inhibition |
|---|---|---|---|---|
| Lactococcus lactis | SL2 | 37 | MRS | +++ |
| Lactobacillus heliveticus | N 2 | 37 | MRS | +++ |
|  | N 258 | 37 | MRS | +++ |
|  | N 262 | 37 | MRS | +++ |
|  | N 271 | 37 | MRS | +++ |
|  | LBL 4 | 37 | MRS | ++++ |
| Lactobacillus delbrueckii subsp. lactis | N 9 | 37 | MRS | ++ |
|  | N 62 | 37 | MRS | ++ |
| Lactobacillus delbrueckii subsp. bulgaricus | LFi 1 | 37 | MRS | +++ |
|  | LFi 5 | 37 | MRS | +++ |
|  | YL 5 | 37 | MRS | +++ |
|  | YL 18 | 37 | MRS | +++ |
| Lactobacillus delbrueckii subsp. delbrueckii | N 8 | 37 | MRS | +++ |
|  | N 187 | 37 | MRS | +++ |
| Lactobacillus acidophilus | La 3 | 37 | MRS | +++ |
|  | La 10 | 37 | MRS | ++ |
|  | La 27 | 37 | MRS | ++ |
|  | La 28 | 37 | MRS | ++ |
| Lactobacillus johnsonii | LA 1 | 30 | MRS | ++ |
| Lactobacillus plantarum | 60 | 30 | MRS | + |
|  | 3.4 RP | 30 | MRS | + |
| Lactobacillus sake | LSK | 30 | MRS | + |
| Lactobacillus curvatus | 18 | 30 | MRS | ++ |
| Leuconosioc carnosum | LCA 3 | 37 | M17 | ++++ |
| Leuconastoc mesenteroides subsp. mesenteroids | A 74 | 30 | MRS | + |
|  | B 50 | 30 | MRS | + |
| Streptococcus thermophilus | SFi 13 | 37 | Elliber | ++ |
|  | SFi 16 | 37 | Elliber | ++ |
|  | SKi 21 | 37 | Elliber | ++ |
|  | SFi 25 | 37 | Elliber | ++ |
|  | ST 11 | 37 | Elliber | ++ |
|  | ST 1 | 37 | Eliber | ++ |

In Table III, it is noted that the inhibition spectrum of the supernatant is broad in the sense that the degree of inhibition is of about the same level for the different species tested.

The inhibition spectrum of the supernatant of a culture producing the variacin of the invention is also regarded as being broad in the sense that it is not limited to species of lactic acid bacteria but extends to other species of Gram-positive bacteria, in particular to the undesirable or pathogenic bacteria *Listeria innocua, Listeria welhia, Listeria monocytogenes,* and to the spores of the Bacilli, for example, as is attested by the results presented in Table IV below.

TABLE IV

| Species | No. | T (° C.) | Media | Inhibition |
|---|---|---|---|---|
| Enterococcus faecalis subsp. faecalis | J | 37 | Elliber | ++ |
| Enterococcus faectum | D 325 | 37 | Elliber | ++ |
|  | MB 26 | 37 | Elliber | ++ |
| Listeria innocua | 7 | 30 | BHI | +++ |
| Listeria monocytogenes | FSM 122 | 30 | BHI | ++++ |
| Listeria weihia | 2 | 30 | BHI | ++ |
| Bacillus subtilis (spores and vegetative cells) | A 1 | 30 | BHI | +++ |
|  | A 2 | 30 | BHI | ++ |
|  | A 3 | 30 | BHI | ++ |
|  | A 4 | 30 | BHI | ++ |
|  | A 13 | 30 | BHI | +++ |
| Bacillus subtilis (spores and vegetative cells) | A 15 | 30 | BHI | ++ |
|  | 24 | 30 | BHI | ++ |
|  | 152 | 30 | BHI | – |
| Bacillus cereus (spores and vegetative cells) | C 1 | 30 | BHI | ++ |
|  | C 2 | 30 | BHI | ++ |
|  | C 5 | 30 | BHI | ++ |
|  | C 6 | 30 | BHI | ++ |
|  | 79 | 30 | BHI | ++++ |
|  | C 15 | 30 | BHI | + |
| Bacillus amyloliquefactens | 226 | 30 | BHI | ++++ |
| Bacillus polymyxa | 252 | 30 | BHI | ++++ |
| Bacillus liqueniformis | 64 | 30 | BHI | ++++ |
| Bacillus stearothermophilus | 10 | 30 | BHI | – |
| Bacillus circulans | 15 | 30 | BHI | ++++ |
| Bacillus pumubus (spores and vegetative cells) | B 1 | 30 | BHI | ++ |
|  | B 2 | 30 | BHI | +++ |
|  | 213 | 30 | BHI | ++++ |
| Clostridium botulinum (spores and vegetative cells) | 100003 | 45 | DRMC | ++ |
|  | 100006 | 45 | DRMC | ++ |
|  | 100019 | 45 | DRMC | ++ |
|  | 100023 | 45 | DRMC | ++ |
| Clostridium butyricum (spores and vegetative cells) | 102001 | 45 | DRMC | ++ |
| Clostridium tyrobutyricum (spores and vegetative cells) | 107002 | 45 | DRMC | + |
| Clostridium perfringens (spores) | 103001 | 45 | DRMC | + |
| Clostridium sporogenes (spores and vegetative cells) | 104001 | 45 | DRMC | + |
| Clostridium acetobutilycum (spores and vegetative cells) | 105001 | 45 | DRMC | + |
| Clostridium thermosaccharolyticum (spores and vegetative cells) | 105001 | 45 | DRMC | + |
| Staphylococcus aureus | 3 | 30 | BHI | + |
|  | 15 | 30 | BHI | + |
|  | 44 | 30 | BHI | + |
|  | 60 | 30 | BHI | ++ |
| Staphylococcus xylosus | 1 | 30 | BHI | + |
| Staphylococcus stimulans | 1 | 30 | BHI | + |
| Staphylococcus carnosus | 1 | 30 | BHI | ++ |
|  | 14 | 30 | BHI | ++ |
| Staphylococcus saprophyticus | 1 | 30 | BHI | + |
|  | 15 | 30 | BHI | + |
| Staphylococcus warneri | 1 | 30 | BHI | + |
| Staphylococcus colvii | 3 | 30 | BHI | + |

The results shown in Table IV make it possible, inter alia, to forecast attractive uses for this supernatant, or for the purified variacin, as an additive in the preparation of foodstuffs, in the role of an agent which is active against pathogenic bacteria, in particular against Clostridia in meat products, against *Listeria monocytogenes* in cheeses, against *Bacillus cereus* and Listeria in dessert mousses, or against the Bacilli in fresh pastes or sauces for fresh pastes, from precisely which bacteria, for example, the above strains originate.

Finally, variacin does not exert any inhibitory effect on the growth of Gram-negative bacteria as can be noted from the results shown in Table V below.

TABLE V

| Species | No. | T (° C.) | Media | Inhibition |
|---|---|---|---|---|
| E. coli | 1 | 30 | BHI | – |
| Enterobacter chloacae | 72 | 30 | BHI | – |
| Salmonella anatum | XIV/20 | 30 | BHI | – |
| Salmonella typhimurium | XIV/274 | 30 | BHI | – |
| Pseudomonas fluorescens | 3 | 30 | BHI | – |

Inhibition spectrum of a concentrate of the supernatant containing variacin

The procedure is as described above except that the inhibitory effect on the growth of different strains of spores and bacteria is determined which is produced by a supernatant concentrate obtained as described in Example 2.

The same species and subspecies are tested as previously. The results of these tests are presented in Tables VI, VII and VIII below. The strain designation or strain no. indicated is the no. which is attributed to it in the Nestlé collection (Address: NESTEC S.A., Centre de Recherche, Vers-chez-les-Blanc, CH-1000 Lausanne 26, Switzerland). The temperature which is indicated is the incubation temperature during the test. The medium which is indicated is the standard medium favourable to the growth of the strain to be tested.

TABLE VI

| Species | No. | T (° C.) | Media | Inhibition |
|---|---|---|---|---|
| Lactococcus lactis | SL2 | 37 | MRS | +++ |
| Lactobacillus helveticus | N 2 | 37 | MRS | ++++ |
|  | N 258 | 37 | MRS | ++++ |
|  | N 262 | 37 | MRS | ++++ |
|  | N 271 | 37 | MRS | ++++ |
|  | LBL 4 | 37 | MRS | ++++ |
| Lactobacillus delbrueckii subsp. bulgaricus | LFi 1 | 37 | MRS | ++++ |
|  | LFi 5 | 37 | MRS | ++++ |
|  | YL 5 | 37 | MRS | ++++ |
|  | YL 18 | 37 | MRS | ++++ |
| Lactobacillus delbrueckii subsp. lactis | N 9 | 37 | MRS | +++ |
|  | N 62 | 37 | MRS | +++ |
| Lactobacillus delbrueckii subsp. delbrueckii | N 8 | 37 | MRS | ++++ |
|  | N 187 | 37 | MRS | ++++ |
| lactobacillus acidophilus | La 3 | 37 | MRS | ++++ |
|  | La 10 | 37 | MRS | ++++ |
|  | La 27 | 37 | MRS | +++ |
|  | La 28 | 37 | MRS | +++ |
| Lactobacillus johnsonii | LA 1 | 30 | MRS | +++ |
| Lactobacillus plantarum | 60 | 30 | MRS | ++ |
|  | 3.4 RP | 30 | MRS | ++ |
| Lactobacillus sake | LSK | 30 | MRS | +++ |
| Lactobacillus curvatus | 18 | 30 | MRS | +++ |
| Leuconostoc carnosus | LCA 3 | 37 | M 17 | ++++ |
| Leuconostoc mesenteroides subsp. mesenteroides | A 74 | 30 | MRS | ++ |
|  | B 50 | 30 | MRS | ++ |
| Streptococcus thermophilus | SFi 13 | 37 | Elliber | +++ |
|  | SFi 16 | 37 | Elliber | +++ |
|  | SFi 21 | 37 | Elliber | +++ |
|  | SFi 25 | 37 | Elliber | +++ |
|  | ST 1 | 37 | Elliber | +++ |
|  | ST 11 | 37 | Elliber | +++ |

TABLE VII

| Species | No. | T (° C.) | Media | Inhibition |
|---|---|---|---|---|
| Enterococcus faecalis subsp. faecalis | J | 37 | Elliber | +++ |
| Enterococcus faecium | D 325 | 37 | Elliber | +++ |
|  | MB 26 | 37 | Elliber | +++ |
| Listeria inaocua | 7 | 30 | BHI | ++++ |
| Listeria monoctogenes | FSM 122 | 30 | BHI | ++++ |
| Listeria weihta | 2 | 30 | BHI | ++++ |
| Bacillus subtilis (spores and vegetative cells) | A 1 | 30 | BHI | +++ |
|  | A 2 | 30 | BHI | ++ |
|  | A 3 | 30 | BHI | ++ |
|  | A 4 | 30 | BHI | ++ |
|  | A 13 | 30 | BHI | +++ |
|  | A 15 | 30 | BHI | ++ |
|  | 24 | 30 | BHI | ++ |
|  | 152 | 30 | BHI | – |
| Bacillus cereus (spores and vegetative cells) | C 1 | 30 | BHI | ++ |
|  | C 2 | 30 | BHI | ++ |
|  | C 5 | 30 | BHI | ++ |
|  | C 6 | 30 | BHI | ++ |
|  | 79 | 30 | BHI | ++++ |
|  | C 15 | 30 | BHI | + |
| Bacillus amyloliquefactens | 226 | 30 | BHI | ++++ |
| Bacillus polymyxa | 252 | 30 | BHI | ++++ |
| Bacillus liqueniformis | 64 | 30 | BHI | ++++ |
| Bacillus stearothermophilus | 10 | 30 | BHI | – |
| Bacillus circulans | 215 | 30 | BHI | ++++ |
| Bacillus pumulus (spores and vegetative cells) | B 1 | 30 | BHI | ++ |
|  | B 2 | 30 | BHI | +++ |
|  | 213 | 30 | BHI | ++++ |
| Clostridium butyricum (spores and vegetative cells) | 102001 | 45 | DRMC | +++ |
| Clostridium perfringens (spores) | 103001 | 45 | DRMC | ++ |
| Clostridium tyrobutyricum (spores and vegetative cells) | 107002 | 45 | DRMC | ++ |
| Clostridium sporogenes (spores and vegetative cells) | 104001 | 45 | DRMC | ++ |
| Clostridium acetobutilycum (spores and vegetative cells) | 106001 | 45 | DRMC | ++ |
| Clostridium thermosaccharolyricum (spores and vegetative cells) | 105001 | 45 | DRMC | ++ |
| Clostridia botulimum (spores and vegetative cells) | 100003 | 45 | DRMC | +++ |
|  | 100006 | 45 | DRMC | +++ |
|  | 100019 | 45 | DRMC | +++ |
|  | 100023 | 45 | DRMC | +++ |
| Staphylococcus aureus | 3 | 30 | BHI | ++ |
|  | 15 | 30 | BHI | ++ |
|  | 44 | 30 | BHI | + |
|  | 60 | 30 | BHI | +++ |
| Staphylococcus xylosus | 1 | 30 | BHI | + |
| Staphylococcus simulans | 1 | 30 | BHI | + |
| Staphylococcus carnosus | 1 | 30 | BHI | +++ |
|  | 14 | 30 | BHI | +++ |
| Staphylococcus saprophyticus | 1 | 30 | BHI | ++ |
|  | 15 | 30 | BHI | ++ |
| Staphylococcus warneri | 1 | 30 | BHI | ++ |
| Staphylococcus cohnti | 3 | 30 | BHI | ++ |

TABLE VIII

| Species | No. | T (° C.) | Media | Inhibition |
|---|---|---|---|---|
| E. coli | 1 | 30 | BHI | – |
| Enterobacter chloacae | 72 | 30 | BHI | – |
| Salmonella anatum | XIV/20 | 30 | BHI | – |
| Salmonella typhimirium | XIV/274 | 30 | BHI | – |
| Pseudomonas fluorescens | 3 | 30 | BHI | – |

The results shown in Tables VI, VII and VIII demonstrate the increased efficacy of the supernatant concentrate, as compared with the supernatant, in inhibiting the growth of many of the strains tested. Inhibition spectra are observed for the same species and subspecies, but at a higher level of inhibition.

This suggests the preparation of a variacin supernatant concentrate, as described in Example 2, and its use for combining pathogenic bacteria in the preparation, for example, of foodstuffs and cosmetics.

Resistance to pH

The agar well test is used to determine whether the variacin which has been isolated in accordance with the present invention is pH-dependent.

To this end, the agar is inoculated with an indicator strain, as previously described in the "agar well test". *Lactobacillus helveticus* (N 2) is used as the indicator strain.

The pH of an extract of the concentrate of the culture supernatant described in Example 2 is adjusted to a pH of from 2 to 10 with 2N NaOH and/or 2N HCl, the extract is incubated at 37° C. for 60 min and the pH is then readjusted to 6–7 before a sample of the extract is deposited in the agar well test well.

A control, using the same supernatant concentrate as pH 7, is set up in parallel and incubated at 37° C. for 60 min before the control sample is deposited in the agar well test well so as to compare the inhibition halos of the test samples with the inhibition halo of the control. The diameter of the inhibition halo of the control is 27 mm.

In Table IX, as in Tables X and XI, the numeral 27 indicates that there is still a halo of 27 mm, corresponding to the full bactericidal activity of the variacin.

TABLE IX

| pH | Inhibition halos |
| --- | --- |
| 2 | 27 |
| 4 | 27 |
| 6 | 27 |
| 8 | 27 |
| 10 | 27 |

The results shown in the above table demonstrate that the bactericidal activity of the variacin is not compromised. It is therefore possible to conclude that the bactericidal activity of variacin is not pH-dependent.

Resistance to heat

The agar well test is used to determine whether the variacin which has been isolated in accordance with the present invention is heat-dependent.

To this end, the agar is inoculated with an indicator strain, as previously described in the agar well test. *Lactobacillus helveticus* (N 2) is used as the indicator strain.

A concentrate extract of the culture supernatant, described in Example 2 and adjusted to pH 7, is incubated at 100° C. for 15 to 60 min before a sample of it is deposited in the agar well test well.

A control, obtained using the same supernatant concentrate at pH 7, is set up in parallel and incubated at 37° C. for 60 min. This enables the inhibition halos of the temperature test samples to be compared with the inhibition halo of the control. The diameter of the inhibition halo of the control is 27 mm.

TABLE X

| Temperature (° C.) | Incubation time (min) | Inhibition halos (mm) |
| --- | --- | --- |
| 100 | 15 | 27 |
| 100 | 30 | 27 |
| 100 | 60 | 27 |

These results demonstrate that variacin is not heat-dependent. Thus, the bactericidal activity of variacin is not compromised even after a 60 min incubation at 100° C.

The resistance of variacin to heat is a biochemical characteristic which is of great importance in relation to using variacin in the preparation of foodstuffs and cosmetics. Thus, variacin can be used, in particular in crude extract or purified form, in the preparation of pasteurized foodstuffs, so as to combat the growth of spores, such as, for example, the Bacilli, which are resistant to heat.

Resistance to heat and to pH

In addition, the stability of variacin is tested when combining pH and heat.

To this end, the agar is inoculated with an indicator strain, as previously described in the "agar well test". *Lactobacillus helveticus* (N 2) is used as the indicator strain.

The culture supernatant concentrate extract described in Example 2 is adjusted to pH 4 or 7 with 2N HCl and/or 2N NaOH and incubated at 115° C. for 20 min; the pH of the extract is then readjusted to 6–7 before a sample of it is deposited in the agar well test well.

A control, obtained at pH 7, is set up in parallel at 37° C. for 20 min, before depositing the control sample in the agar well test well so as to compare the inhibition halos of the test samples with the inhibition halo of the control. The diameter of the inhibition halo of the control is 27 mm.

TABLE XI

| pH | Incubation time (min) | Incubation temperature (° C.) | Inhibition halo (mm) |
| --- | --- | --- | --- |
| 4 | 20 | 115 | 27 |
| 7 | 20 | 115 | 27 |

The results given in the above table demonstrate that the bactericidal activity of variacin is not compromised at pH 4 or 7, combined with an elevated temperature.

Purification of variacin 4 l of BHI medium are inoculated with a culture of *Micrococcus varians,* which culture produces the variacin according to the present invention. This standard culture is incubated at 30° C. overnight under aerobic conditions and while shaking, after which it is centrifuged at 5000 g so as to collect the supernatant in a recipient vessel, to which 72 g of XAD-7 resin (Amberlite (R)) are added.

The mixture is stirred at 25° C. for 30 min in order to facilitate adhesion of the variacin molecules to the resin, and the whole is then transferred onto a sintered glass there the supernatant is filtered in vacuo.

The resin is washed successively in 3 buffers containing 20 mM sodium citrate, pH 4, and isopropanol. The first buffer contains 10% isopropanol, the second buffer contains 15% isopropanol, and the third buffer contains 20% isopropanol.

The resin is transferred into a column and the variacin is eluted with 700 ml of buffer containing 20 mM sodium citrate, pH 4, and 25% isopropanol. The bactericidal activity of the variacin is monitored using the agar well test as described previously.

The active fractions are mixed and the isopropanol is evaporated. A 5 ml S-Resource column for FPLC (Pharmacia) is prepared by equilibrating it with 20 mM sodium citrate buffer. The evaporated mixture of active fractions is loaded onto this column and the contents of the column are then eluted with an NaCl buffer having a gradient of from 100 mM to 400 mM.

Fractions are collected and the bactericidal activity of the variacin, which has thus been purified, is checked using the agar well test.

Sequencing the variacin

The N-terminal part of the variacin purified from strains CNCM I-1586 and CNCM I-1587 is sequenced using an Applied Biosystems 4774 automatic sequencer. This reveals the peptide sequence of 5 amino acids whose sequence is identical to that for the N-terminal part of the sequence SEQ ID NO:1, described in the sequence list below. It was not possible to demonstrate the presence of a peptide of more than 5 amino acids during the sequencing.

In addition, variacin which has been purified from strains CNCM I-1586 and CNCM I-1587 is hydrolysed with 6N HCl for 10 min. 3 peptides are obtained which are isolated in the usual manner by HPLC. It was only possible to sequence one of the three peptides which were isolated since the other two most probably contain peptide modifications. The sequence of the said peptide which was isolated in this way is identical to that comprising amino acids 19 to 22 of the sequence SEQ ID NO:1, described in the sequence list below.

Finally, a fraction containing the variacin which has been purified from strains CNCM I-1586 and CNCM I-1587 is subjected to mass spectrometry and the variacin is found to have a molecular weight of 2659 daltons.

Homology

Homology was demonstrated between the sequence of lacticin 481 from *Lactococcus lactis* and that of the variacin according to the present invention. This homology relates, in particular, to the sequences of the N-terminal part of the two bacteriocins. Thus, amino acids 1 to 5 of the N-terminal sequence of variacin are identical to amino acids 3 to 7 of the sequence SEQ ID NO:8 of lacticin 481, described in the sequence list below. Nevertheless, it is only a matter of partial homology and not of identity.

In addition, secreted lacticin 481 is shown by mass spectrometry to have a molecular weight of 2900 daltons, whereas the molecular weight of secreted variacin is 2659 daltons, as we have previously seen.

When the strain of *Lactococcus lactis* which produces lacticin 481 is inoculated in the presence of a variacin extract, as previously described in the inhibition spectrum test, the growth of the said strain is seen to be inhibited. The strain of *Lactococcus lactis* which produces lacticin 481 is immune to its own bacteriocin, lacticin 481, but is not immune to the variacin which is produced by either of the two *Micrococcus varians* strains according to the present invention. These results, which were obtained in the previously described inhibition spectrum test, confirm that these two bacteriocins are different.

The above genetic findings demonstrate that while lacticin 481 and variacin exhibit sequence homologies, their sequences are not identical. The biochemical findings, as well as the microbiological findings, confirm that lacticin 481 and variacin are two different bacteriocins.

Sequencing the variacin gene

The degenerate nucleotide sequence SEQ ID NO:4, which is described in the sequence list below and which corresponds to the C-terminal part of the peptide of the previously sequenced variacin, is constructed in a conventional manner. The mixture of SEQ ID NO:4 sequences is then rendered radioactive by the action of T4 polynucleotide kinase.

A preparation of chromosomal DNA is made from strains CNCM I-1586 and CNCM I-1587 in a conventional manner. The said DNA preparation is digested with SalI, SacI, SphI and BamHI in accordance with the recommendations of the enzyme suppliers, 2 μg of the digestion product are then run on an agarose gel. The DNA on the gel is washed with 250 mM HCl and the migration product is then transferred, in alkaline medium, from the gel onto a "Zetaprobe" (Biorad) membrane. The Zetaprobe membrane is then prehybridized at a temperature of 55° C., which temperature is lowered by 5° C. every 2 h down to a temperature of 40° C., in a medium comprising 6× SSC, 1% SDS and 0.25% skimmed milk. This membrane is hybridized with the degenerate radioactive probe exhibiting the sequence SEQ ID NO:4 in the previous hybridization medium and under the same temperature conditions. It is then left to incubate at 40° C. for 4 hours, after which the membrane is washed at 40° C. in 6× SSC. Finally, it is exposed on an autoradiography film at −80° C. for 16 h.

The hybridization demonstrates a variety of migration bands: a SalI band of 7 kb, a SacI band of 1.4 kb, a BamHI band of 1.8 kb and an SphI band of greater than 15 kb.

5 μg of genomic DNA from strain CNCM I-1586 is then digested with the restriction enzyme BamHI and a fragment of 1.6–2 kb is separated by agarose gel chromatography followed by elution of that part of the gel containing the fragment. The eluted DNA fragment is ligated to the vector pK 19 (Gene, 56 (1987)309–312), which has previously been digested with BamHI and then treated with calf intestinal phosphatase (Boehringer Mannheim, part No. 713023).

The *Escherichia coli* BZ 234 (Biozentrum collection—University of Basle, Switzerland), which has previously been rendered competent, is then transformed, in a conventional manner, with the ligation medium. The clones containing the insert are identified on agar medium which is supplemented with 50 μg/ml kanamycin, 60 ng/ml IPTG (Boehringer Mannheim, part No. 724815) and 300 ng/ml X-gal (Boehringer Mannheim, part No. 651745) and which is incubated at 37° C. for 16 h.

The white colonies, which normally contain an insert, are picked out into 96-well microtitre plates. Each white colony is picked out into one of the said wells, with each well containing 150 μl of LB medium supplemented with 50 μg/ml kanamycin, and incubated at 37° C. for 20 h in order to produce mini cultures.

Two primers of opposite orientation are prepared because the orientation of the gene in vector pK 19 is not known. To this end, the said primers are constructed by assembling them from a nucleotide fragment exhibiting the sequence SEQ ID NO:5, partially encoding lacticin 481, which is linked to one or other of the universal probes of the pUC vectors, which probes exhibit the sequence SEQ ID NO:6 or the sequence SEQ ID NO:7.

1 μl from each well is mixed with 100 pmol of one of the said primers, 6 μl of 2 mM dNTPs and 2.5 μl of Taq buffer (P. H. Stehelin & Cie AG, cat. no. TP05b), and the whole is covered with a drop of Dyna-wax (Finnzymes Oy, 02201 Espoo, Finland) and heated at 98° C. for 10 min so as to lyse the bacteria; the PCR is then carried out.

The positive clones then give a band of 800 bp on an electrophoresis gel.

The positive clones are selected in this way and the plasmid DNA of these clones is extracted; the DNA fragment which is cloned into the pK 19 vector is then sequenced by the dideoxynucleotide method using a sequencing kit (Pharmacia Biotech, part No. 27-1682-01) and universal primers, followed by specific primers which are based on the sequence thus obtained.

This results in a nucleotide sequence, SEQ ID NO:2, which is described in the sequence list below, being obtained. The said nucleotide sequence encodes the sequence SEQ ID NO:1, which corresponds to the amino acid sequence of variacin, prior to maturation.

Variants of the protein conserving the bactericidal activity

Variants of the protein having the amino acid sequence SEQ ID NO:1 are created. To this end, the encoding DNA sequence of the variacin without the peptide signal (recombinant vector pK19 above) is inserted into the polyclonal site of plasmid pKK232-8 (Pharmacia, UK). Chemical mutagenesis with hydroxylamine are performed on the expression vector according to the process described by Yoast et al. (Applied and Env. Micro., 60, 1221–1226, 1994). Other methods could also be used, such as the method described by Dunn et al. (Protein Engineering, 2, 283–291, 1988) dealing with the creation of precise mutations. The mutagenized vectors are transferred into competent *E. coli* BZ 234 and transformants are selected. Transformants are isolated and cultivated. Supernatants are prepared and concentrated according to Example 2. Each supernatant is then screened according to the "agar well test" described above. Results show that some supernatants provide an inhibition activity against Lactobacillus, Lactococcus, Streptococcus, Enterococcus, Listeria, Bacillus, Clostridia and/or Staphylococcus, for example. DNA analysis of vectors expressing the bacteriocin show that some bacteriocins present a DNA sequence which is different to the encoding sequence SEQ ID NO:2. The amino acid sequence of these variants are generally different by from 1 to 4 amino acids.

The Examples below are presented by way of illustrating the process for producing, and the uses of, the bacteriocin according to the present invention. The percentages in the examples are given by weight unless otherwise indicated.

EXAMPLE 1

BHI culture medium is inoculated, and a culture containing organisms of the *Micrococcus varians* strain is added to it. The whole is incubated overnight at 30° C. with shaking and under aerobic conditions, after which the medium contains $10^8$ organisms of the strain per ml. The standard culture thus obtained is centrifuged. The standard supernatant is collected.

EXAMPLE 2

The supernatant concentrate is obtained from 750 ml of the said supernatant, which has been obtained as described in Example 1 and to which is added 15 g of XAD-7 resin (Amberlite (R)). The mixture is shaken at 4° C. for 60 min and is then filtered through a No. 604 Schleicher & Schuell (Germany) filter. The filter is then washed with 1% sodium citrate in order to elute all the non-adsorbed proteins. The resin is isolated and transferred into a recipient vessel containing sodium citrate and the whole is shaken for 2 min. The resin, together with the sodium citrate, is transferred into a column and the sodium citrate is eluted with 50% acetonitrile and 0.1% TFA. The eluate is evaporated and the residue is resuspended in 50 mM phosphate buffer at pH 6.8.

EXAMPLE 3

10 liters of a culture of the *Micrococcus varians* strain are produced in BHI medium overnight at 30° C. with shaking and under aerobic conditions. 200 g of XAD-7 resin (Amberlite) are then added directly to the culture and the whole is shaken gently at 4° C. for 1 h. The mixture is then filtered through a No. 604 Schleicher & Schuell (Germany) filter, and the resin which is retained on the filter is then washed with 10 liters of a 50 mM acetic acid, pH 5.2, solution in order to remove the bacteria. After that, 450 ml of a solution containing 100% ethanol and 20 mM ammonium acetate are added to the resin and the whole is filtered in order to remove the resin; the filtrate is then lyophilized in order to obtain a powder containing the variacin according to the invention, which can be used in the foodstuff industry.

The bactericidal activity of this powder, which has been previously diluted in water, is then determined by means of the previously described agar well test. This powder possesses at least $10^5$ au/g powder.

Finally, the above powder is added, at the rate of 0.5 g/kg, to a meat foam while it is being prepared in a traditional manner. This results in a meat foam, each g of which contains 50 au of bacteriocins which are able to completely inhibit the development of pathogenic bacteria, in particular Clostridia.

EXAMPLE 4

This example relates to the preparation of a moisturizing cream for skin care containing the powder described in Example 3 at the rate of 0.05 g/kg, that is, therefore, variacin, which is capable of inhibiting the development of undesirable bacteria on the skin, in particular *Staphylococcus aureus* and *Streptococcus pyogenes*, at the rate of 5 au/g.

In order to prepare this emulsion, the components of lipid phase A are mixed and heated at 75° C. Aqueous phase B is prepared and also heated at 75° C.; lipid phase A is then added, while mixing slowly, and, after that, the whole is cooled, under slow mixing, down to ambient temperature, that is approximately 25° C. The C constituents are added slowly, at this temperature, in the order of the formula.

|  | % |
|---|---|
| Lipid phase A |  |
| Peg-6 stearate, glycerate and peg-20-cethyl ether (peg: polyethylene glycol) | 15 |
| liquid paraffin | 5 |
| Wheat germ oil stabilized with 0.1% phenylindane (antioxidant) and 1% soybean phospholipid (see EP94109355.1) | 3 |
| Sweet-almond oils | 2 |
| Cetyl alcohol | 1 |
| Isostearyl isostearate | 2 |
| 2-Octyldodecyl myristate | 1 |
| Lanolin wax |  |
| Aqueous phase B |  |
| Methylisothiazoline | 0.1 |
| Demineralized water | 59.6 |
| Human placenta protein | 2 |
| C Additives |  |
| Propylene glycol and calendula extract | 2 |
| 50% soluble collagen in demineralized water | 5.8 |
| Perfume | 0.3 |
| 2.5% bacteriocin powder in accordance with Ex. 3 in demineralized water | 0.2 |

EXAMPLE 5

The bacteriocin powder described in Example 3 is added to a mouthwash at the rate of 0.5 g/kg. This mouthwash is consequently capable of inhibiting the development of pathogenic bacteria, in particular *Streptococcus sobrinus, Streptococcus sanguis, Steptococcus mutans* and *Actinomyces viscosus,* in the buccal cavity.

EXAMPLE 6

A solution comprising the bacteriocin powder of Example 3, which is diluted in water at the rate of 1%, is sprayed onto a foodstuff which is intended to be sterilized in order to prevent post-contamination during packaging.

We claim:

1. A process for preparing a composition having bactericidal activity against bacteria including *Listeria monocytogenes* comprising:

culturing cells of a strain of *Micrococcus varians* selected from the group consisting of strain CNCM I-1586 and strain CNCM I-1587 to obtain cultured cells in a concentration of from $10^7$ to $10^{11}$ organisms per ml of the medium and a supernatant comprising the bacteriocin; and separating the supernatant form the cultured cells to obtain a supernatant composition comprising the bacteriocin.

2. A process according to claim 1 further comprising isolating the bacteriocin from the supernatant composition to obtain a purified bacteriocin product.

3. A process according to claim 2 further comprising lyophilizing the purified bacteriocin product to obtain a lyophilized product.

4. A process according to claim 1 further comprising concentrating the supernatant composition to obtain a concentrate comprising the bacteriocin.

5. A process according to claim 4 further comprising drying the concentrate to obtain a powder comprising the bacteriocin.

6. The supernatant composition of the process of claim 1.

7. The purified bacteriocin product of the process of claim 2.

8. The lyophilized product of the process of claim 3.

9. The concentrate of the process of claim 4.

10. The powder of the process of claim 5.

* * * * *

UNITED STATES PATENT AND TRADEMARK OFFICE
CERTIFICATE OF CORRECTION

PATENT NO. : 6, 150, 139
DATED : November 21, 2000
INVENTOR(S) : Beat MOLLET, *et al.*

It is certified that error appears in the above-identified patent and that said Letters Patent is hereby corrected as shown below:

On the title page in the section "[75] Inventors", change "Suri Brono" to -- Bruno Suri --.

Column 21, line 36, (line 10 of claim 1), change "form" to -- from --.

Signed and Sealed this

Eighth Day of May, 2001

*Attest:*

NICHOLAS P. GODICI

*Attesting Officer*    *Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 25 amino acids
       (B) TYPE: amino acid
       (C) STRANDEDNESS:
       (D) TOPOLOGY: linear (ii) MOLECULE TYPE: protein (vi) ORIGINAL SOURCE:
       (A) ORGANISM: MICROCOCCUS VARIANS
       (C) INDIVIDUAL ISOLATE: TWO CLONES CNCM I-1586 and CNCM
           I-1587

(xi) SEQUENCE DESCRIPTION: SEQ ID NO:1:

Gly Ser Gly Val Ile Pro Thr Ile Ser His Glu Cys His Met Asn Ser
1               5                   10                  15

Phe Gln Phe Val Phe Thr Cys Cys Ser
            20                  25

(2) INFORMATION FOR SEQ ID NO:2:

(i) SEQUENCE CHARACTERISTICS:
       (A) LENGTH: 278 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: MICROCOCCUS VARIANS
       (C) INDIVIDUAL ISOLATE: TWO CLONES CNCM I-1586 and CNCM
           I-1587

(ix) FEATURE:
       (A) NAME/KEY: CDS
       (B) LOCATION: 88..228

(ix) FEATURE:
       (A) NAME/KEY: sig_peptide
       (B) LOCATION: 88..153

(ix) FEATURE:
       (A) NAME/KEY: mat_peptide
       (B) LOCATION: 154..228

(xi) SEQUENCE DESCRIPTION: SEQ ID NO:2:

GTTGAAAATC ATCCGGAAGG ATGATTCTGT GTTCATGCGA GGCCACCCGG AATCGCGGCA      60

GCCACACCCA CTGAGAGGAC TAGAACA ATG ACG AAC GCA TTT CAG GCA CTG        111
                              Met Thr Asn Ala Phe Gln Ala Leu
                              -22     -20             -15

GAC GAA GTC ACG GAC GCC GAG CTC GAC GCC ATC CTT GGC GGG GGC AGT      159
Asp Glu Val Thr Asp Ala Glu Leu Asp Ala Ile Leu Gly Gly Gly Ser
            -10             -5                      1

GGT GTT ATT CCC ACG ATC AGC CAC GAG TGC CAC ATG AAC TCC TTC CAG      207
Gly Val Ile Pro Thr Ile Ser His Glu Cys His Met Asn Ser Phe Gln
        5                   10                  15

TTC GTG TTC ACC TGC TGC TCC TGAGAAACTC CTCCGATGCT CAGAGGGCCG         258
Phe Val Phe Thr Cys Cys Ser
        20              25

CGCTAGGAAA ATCTAGTAAG                                                                        278

(2) INFORMATION FOR SEQ ID NO:3:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:3:

Met Thr Asn Ala Phe Gln Ala Leu Asp Glu Val Thr Asp Ala Glu Leu
-22     -20             -15             -10

Asp Ala Ile Leu Gly Gly Gly Ser Gly Val Ile Pro Thr Ile Ser His
    -5          1               5                       10

Glu Cys His Met Asn Ser Phe Gln Phe Val Phe Thr Cys Cys Ser
                15              20                  25

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (xi) SEQUENCE DESCRIPTION: SEQ ID NO:4:

TGGCARTTYG TNTTYACNTG YTG                                                                     23

(2) INFORMATION FOR SEQ ID NO:5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

GGNTCNGGNG TNATHCAYAC NATHTCNCAY GARTGYAAYA TGAA                                               44

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

ATAACAATTT CACACAGG                                                                           18

(2) INFORMATION FOR SEQ ID NO:7:

(i) SEQUENCE CHARACTERISTICS:
        (A) LENGTH: 18 base pairs
        (B) TYPE: nucleic acid -continued

```
         (C) STRANDEDNESS: single
         (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:7:

GGTTTTCCCA GTCACGAC                                                    18

(2) INFORMATION FOR SEQ ID NO:8:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:8:

Lys Gly Gly Ser Gly Val Ile
1               5
```